United States Patent [19]
Padda et al.

[11] Patent Number: 5,395,320
[45] Date of Patent: Mar. 7, 1995

[54] PROGRAMMABLE INFUSION PUMP WITH INTERCHANGEABLE TUBING

[75] Inventors: Shan Padda; Doron Levitas; Arie Kalo, all of Chicago, Ill.

[73] Assignee: Sabratek Corporation, Niles, Ill.

[21] Appl. No.: 150,551

[22] Filed: Nov. 9, 1993

Related U.S. Application Data

[63] Continuation of Ser. No. 895,716, Jun. 9, 1992, abandoned.

[51] Int. Cl.⁶ .............................................. A61M 5/00
[52] U.S. Cl. .................................... 604/65; 604/153; 128/DIG. 12
[58] Field of Search .................... 604/65, 153, 155; 128/DIG. 12, DIG. 13

[56] References Cited

U.S. PATENT DOCUMENTS

| | | |
|---|---|---|
| 3,685,697 | 8/1972 | Caslow et al. |
| 3,771,694 | 11/1973 | Kaminski . |
| 3,809,871 | 5/1974 | Howard et al. . |
| 3,901,231 | 8/1975 | Olson . |
| 3,908,652 | 9/1975 | Weissinger . |
| 3,985,133 | 10/1976 | Jenkins et al. . |
| 4,085,747 | 4/1978 | Lee . |
| 4,155,362 | 5/1979 | Jess ........................... 604/153 |
| 4,187,057 | 2/1980 | Xanthopoulos . |
| 4,221,543 | 9/1980 | Cosentino et al. ............ 417/22 |
| 4,256,437 | 3/1981 | Brown . |
| 4,276,004 | 6/1981 | Hahn . |
| 4,278,085 | 7/1981 | Shim ........................... 604/153 |
| 4,443,218 | 4/1984 | DeCant, Jr. et al. . |
| 4,457,751 | 7/1984 | Rodler . |
| 4,493,706 | 1/1985 | Borsanyi et al. ............ 604/153 |
| 4,519,792 | 5/1985 | Dawe . |
| 4,529,401 | 7/1985 | Leslie et al. . |
| 4,537,561 | 8/1985 | Xanthopoulos . |
| 4,617,014 | 10/1986 | Cannon et al. . |
| 4,653,987 | 3/1987 | Tsuji et al. . |
| 4,657,490 | 4/1987 | Abbott . |
| 4,664,430 | 5/1987 | Brown et al. . |
| 4,668,220 | 5/1987 | Hawrylenko . |
| 4,685,903 | 8/1987 | Cable et al. . |
| 4,689,043 | 8/1987 | Bisha . |
| 4,690,673 | 9/1987 | Bloomquist . |
| 4,692,145 | 9/1987 | Weyant . |
| 4,714,462 | 12/1987 | DiDomenico . |
| 4,725,205 | 2/1988 | Cannon et al. . |
| 4,728,265 | 3/1988 | Cannon . |
| 4,731,051 | 3/1988 | Fischell . |
| 4,741,736 | 5/1988 | Brown . |
| 4,744,786 | 5/1988 | Hooven . |
| 4,749,109 | 6/1988 | Kamen . |
| 4,752,289 | 6/1988 | Balding et al. . |
| 4,756,706 | 7/1988 | Kerns et al. . |
| 4,758,228 | 7/1988 | Williams . |
| 4,781,548 | 11/1988 | Alderson et al. . |
| 4,785,799 | 11/1988 | Schoon et al. ............... 128/DIG. 12 |
| 4,808,167 | 2/1989 | Mann et al. . |
| 4,838,860 | 6/1989 | Groshong et al. . |
| 4,840,542 | 6/1989 | Abbott . |
| 4,846,637 | 7/1989 | Alderson et al. . |
| 4,850,971 | 7/1989 | Colvin . |
| 4,850,980 | 7/1989 | Lentz et al. . |
| 4,856,339 | 8/1989 | Williams . |
| 4,890,984 | 1/1990 | Alderson et al. . |
| 4,898,578 | 2/1990 | Rubalcaba, Jr. . |
| 4,898,579 | 2/1990 | Groshong et al. . |
| 4,919,650 | 4/1990 | Feingold et al. . |
| 4,936,760 | 6/1990 | Williams . |
| 4,950,136 | 8/1990 | Haas et al. ................... 604/153 |
| 4,978,335 | 12/1990 | Arthur, III . |
| 5,006,050 | 4/1991 | Cooke et al. . |
| 5,013,303 | 5/1991 | Tamari et al. . |
| 5,018,945 | 5/1991 | D'Silva ........................ 604/153 |
| 5,034,004 | 7/1991 | Crankshaw . |
| 5,061,242 | 10/1991 | Sampson . |
| 5,074,756 | 12/1991 | Davis ........................... 604/153 |
| 5,098,261 | 3/1992 | Bertoncini ................... 604/153 |
| 5,116,203 | 5/1992 | Natwick et al. ............. 604/153 |
| 5,211,548 | 5/1993 | Okada .......................... 604/153 |
| 5,213,483 | 5/1993 | Faherty et al. .............. 604/153 |

Primary Examiner—Ralph A. Lewis
Attorney, Agent, or Firm—Stephen C. Glazier

[57] ABSTRACT

An infusion pump which can be programmed to deliver any of a variety of selected profiles of fluid medicine volume delivered over time. The pump can be programmed to accommodate any of a variety of the commonly available sizes and types of disposable tubing. The preferred embodiment uses a variable speed motor, peristaltic fingers, a keyboard, a microprocessor chip with memory, and a motor controller.

9 Claims, 6 Drawing Sheets

PROGRAMMABLE INFUSION PUMP WITH INTERCHANGEABLE TUBING

This is a continuation of patent application Ser. No. 07/895,716, filed Jun. 9, 1992, now abandoned.

BACKGROUND OF THE INVENTION

The field of this invention is medical infusion pumps. More specifically, this invention is an infusion pump which has programmable delivery profiles, and which can be programmed to be used with a variety of intravenous ("IV") infusion sets using various types of tubing with various sizes and physical characteristics that impact delivery profiles.

A variety of infusion pumps and controllers exist in the prior art. Commonly, an IV administration set is used with a disposable reservoir bag and a flexible IV tube. The tubing has within it a drip chamber to eliminate bubbles in the fluid in the tubing. The distal end of the tubing has a intravenous needle for insertion into the patient. Traditionally the reservoir bag is raised above the patient and drained by gravity into the patient.

Infusion pumps and controllers were developed to attach to the outside of the tubing to control the rate of flow from the reservoir bag into the patient. The controllers would constrict the tubing or unconstrict it over time to control the flow by gravity to the patient. Infusion pumps use the power of the pump to move the fluid to the patient and do not use the elevation of the bag above the patient to determine the pressure in the tubing.

Some infusion pumps use a chamber of a known volume. The rate of flow of the pump is controlled by controlling the number of times in a period that the chamber is filled and pumped out.

Many infusion pumps are peristaltic pumps. Peristaltic pumps in the prior art are of two types, finger peristaltic pumps and rotary peristaltic pumps. Finger peristaltic pumps have a row of fingers or depressors along a section of the tubing. The fingers are depressed in a series or waves creating a moving contraction along the tubing which pumps the fluid through the tubing. Rotary peristaltic pumps have a number of arms on a rotor. Each arm has a roller at the end of the arm. As the rotor rotates in a circular chamber, the rollers on the end of the arms roll along and constrict the tubing lining the outer surface of the chamber. This creates a series of rolling contractions through the tubing that pumps the fluid through the tubing.

A primary limitation of the gravity infusion bag is that the pressure (and therefore the flow rate) of the fluid is determined by the height at which the bag is hung above the patient. Furthermore, the prior art peristaltic pumps are calibrated to deliver the requested flow rate for a specific size and type of tubing. Therefore, a different prior art peristaltic pump is required for each tubing size and type.

SUMMARY OF THE INVENTION

The present invention is an infusion pump which can be programmed to deliver any of a variety of selected profiles of fluid medicine volume delivered over time. Furthermore, the present invention can be programmed to accommodate any of a variety of the commonly available sizes and types of disposable tubing with which the invention is used.

The preferred embodiment of the present invention is a finger peristaltic pump to be applied to the tubing of an IV administration set. The fingers are suppressed in a rolling series by a revolving cam adjacent to the fingers and in contact with the fingers inside the pump. The cam can be rotated at different speeds by a variable speed electric motor attached to the cam. By altering the electricity from the power source, whether AC from a wall socket or DC from batteries, the speed of the motor can be controlled. This in turn controls the rate of revolution of the cam, which controls the speed at which the constrictions are created and moved down the tubing by the fingers. This in turn controls the fluid flow rate of the pump. An integrated circuit chip is programmed with the data required for a variety of delivery profiles, and for the flow characteristics of a variety of IV tubing. By operating buttons on a keypad on the invention, the integrated circuits and memories are activated to select the desired flow rate profile, and indicate the type of tubing in use. The chip memory then calculates, from the information in its data base, the rate and timing at which the cam must be rotated over time to provide the required delivery profile of fluid to the patient given the characteristics of the tubing in use. Furthermore, the chip communicates with a pressure sensing strain gauge adjacent to the intravenous tube, (which senses occlusions in the tube) and recalibrates the gauge for different tube types.

This invention for the first time provides an infusion pump that is programmed to deliver a variety of different fluid delivery profiles to the patient, and to be operated with a variety of available tubing types. This eliminates the need for a hospital to have a variety of infusion pumps to operate with a variety of tubing types. This allows superior service to the patient by the selection of a variety of sophisticated and complicated medicine delivery profiles, and provides a lower cost for the hospital since this service may be provided by one pump rather than a variety of pumps.

Examples of different delivery profiles that may be programmed for infusion by the present invention include (1) fixed rate of flow, (2) ramp up (steadily increasing flow rate), (3) ramp down (steadily decreasing flow rate), (4) fixed rate with increased rate spikes at specified intervals, and (5) no flow with an infusion bolus at specified intervals.

BRIEF DESCRIPTION OF THE DRAWINGS

FIG. 5 shows schematically the logic of the microcontroller.

DESCRIPTION OF THE PREFERRED EMBODIMENT

Figure 1:
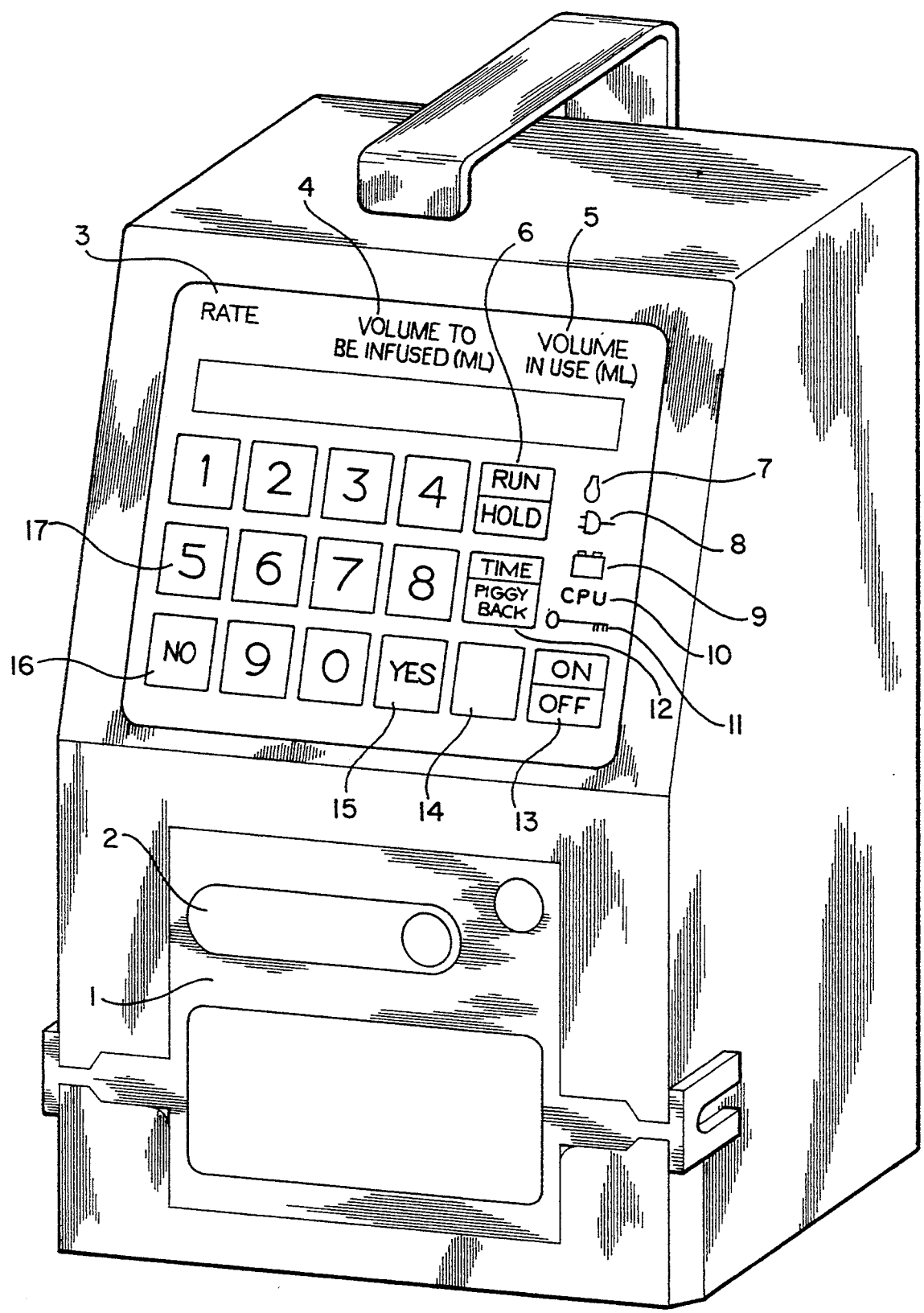
FIG. 1 provides a front view of the preferred embodiment with the door closed.

FIG. 1 shows a front view of the preferred embodiment with the door closed. The outer door 1 is indicated with the outer door latch 2. The instrument further contains an infusion rate display 3, a volume to be infused display 4, a volume infused display 5, a run/hold key 6, an infusion indicator 7, a line power indicator 8, a battery power indicator 9, a CPU malfunction indicator 10, a lockout indicator 11, a time/piggyback key 12, an on/off key 13, a pressure key 14, a yes key 15, a no key 16, and ten numbered keys 17.

The outer door 1 protects the inner door 20. The outer door latch 2 opens the outer door 1 to give access to the inner door 20. The inner door 20 has a spring loading between it and the outer door 1 which is depressed when the doors are closed against the tubing. The infusion rate display 3 indicates in milliliters per hour the rate at which the fluid is being delivered by the pump. The volume to be infused display 4 indicates in milliliters the volume of the fluid to be delivered by the pump. The volume infused display 5 indicates in milliliters the cumulative volume of fluid which has been infused by the pump. The run/hold key 6 is used to start, pause, or restart the infusion, as well as to temporarily silence the audible alarm. The infusion indicator 7 flashes when there is a flow of fluid through the drip chamber in the IV administration set. The line power indicator 8 illuminates when the pump is connected to a power line. The battery power indicator 9 illuminates when the pump is operating on its internal battery. The CPU malfunction indicator 10 illuminates when there is a major internal malfunction. The lockout indicator 11 illuminates when the pump's patient lockout is activated. The time/piggyback key 12 is used to indicate the time for the volume to be infused that is remaining until the end of the infusion. Also, this key is used to access the piggyback mode. The on/off key 13 is used to turn the pump on or off. The pressure key 14 is used to set as well as to indicate the pressure alarm setting at high or low. The yes key 15 is used to answer the pump's prompts and to accept delivery parameters. The no key 16 is used to answer the pump's prompts and to reject delivery parameters. The numbered keys 17 are used to enter the delivery parameters as well as to enter the access code.

Figure 2:
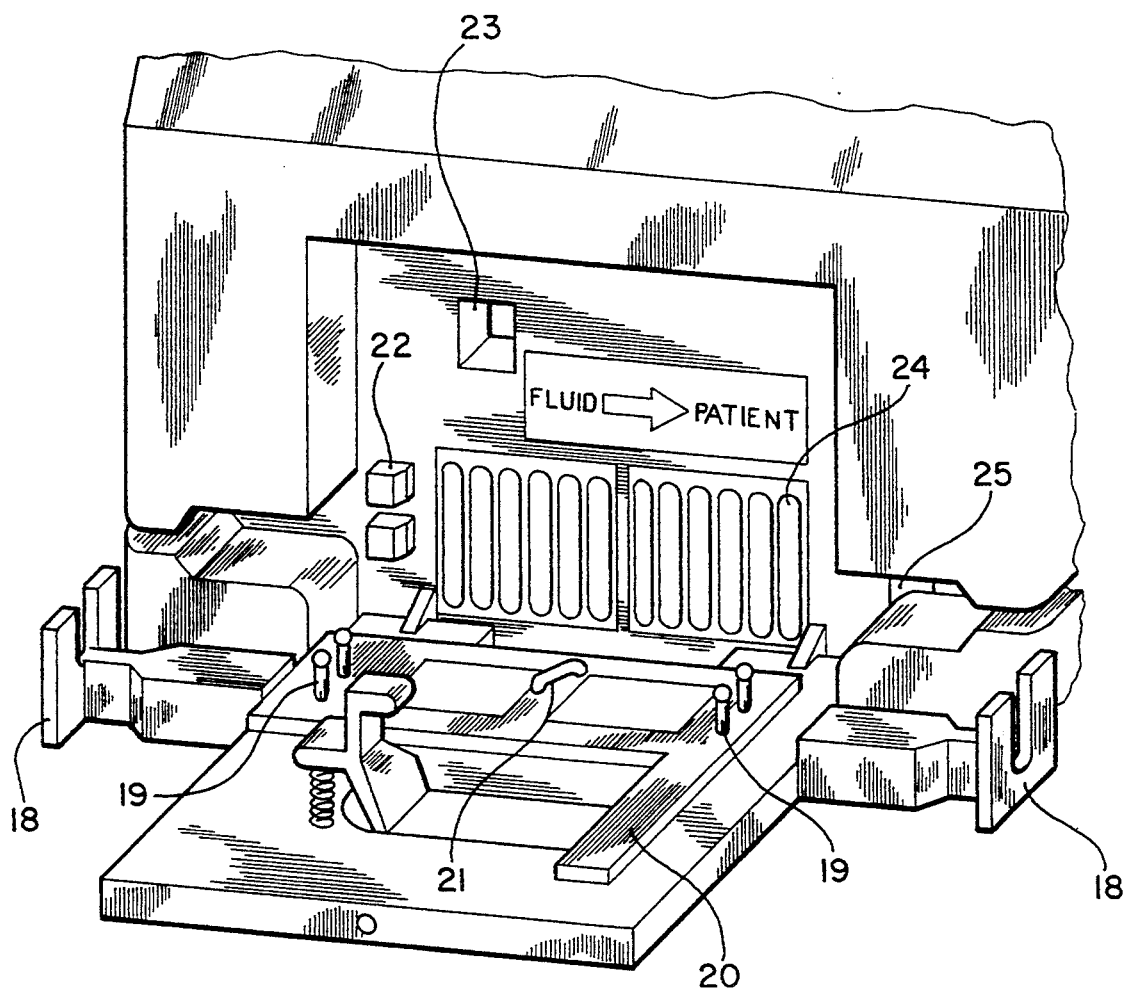
FIG. 2 provides an inner view of the front of the preferred embodiment with the door opened.

FIG. 2 shows the interior view of the preferred embodiment through the open door 1 on the front of the preferred embodiment. Outer tubing guides 18 are shown with inner tubing guides 19, on the interior of the inner door 20. Furthermore, there are shown the free flow clamp 21, the air in line detector 22, the door open sensor 23, the pumping mechanism 24, consisting here of twelve fingers in a series, and a pressure indicator 25.

The outer tubing guides 18 are used to position the IV set's tubing for correct pump operation. The inner tubing guides 19 are used to position the set's tubing for correct pump operation. The inner door 20 presses the tubing against the twelve fingers of the pumping mechanism. In the preferred embodiment the twelve fingers are not spring loaded but are attached to the differential camshaft so that the rotating camshaft pushes and pulls them as it turns. The preferred embodiment uses a DC server motor to control the speed of the differential camshaft. The free flow clamp 21 prevents gravity freeflow when the outer door 1 is open. The air line indicator 22 detects air bubbles in the intravenous administration set. The air in line detector 22 in the preferred embodiment is an ultrasound system. A receiver is on one side of the tube and a transmitter is on the other side of the tube. The signal that is generated is altered by (and therefore detects) any bubble within the tubing between the receiver and transmitter. The door open sensor 23 detects if the outer door 1 is open during an infusion. The door sensor 23 is a simple mechanical switch. The pumping mechanism 24 provides accurate delivery of medicine as described further herein. The pressure sensor 25 monitors the pressure inside the tubing. The pressure sensor 25 in the preferred embodiment is a strain gauge that is pressed against the tubing. When the tube contains pressure it expands, thereby creating a signal in the strain gauge. This is calibrated for each tube type to indicate the pressure that exists at that time. The operator's selection of tubing also activates the integrated circuit chip and the internal memory to select the proper calibration for this pressure sensor. The pressure sensor 25 acts as a blockage sensor, since when the tube is blocked the pressure in it will go up.

Figure 3:
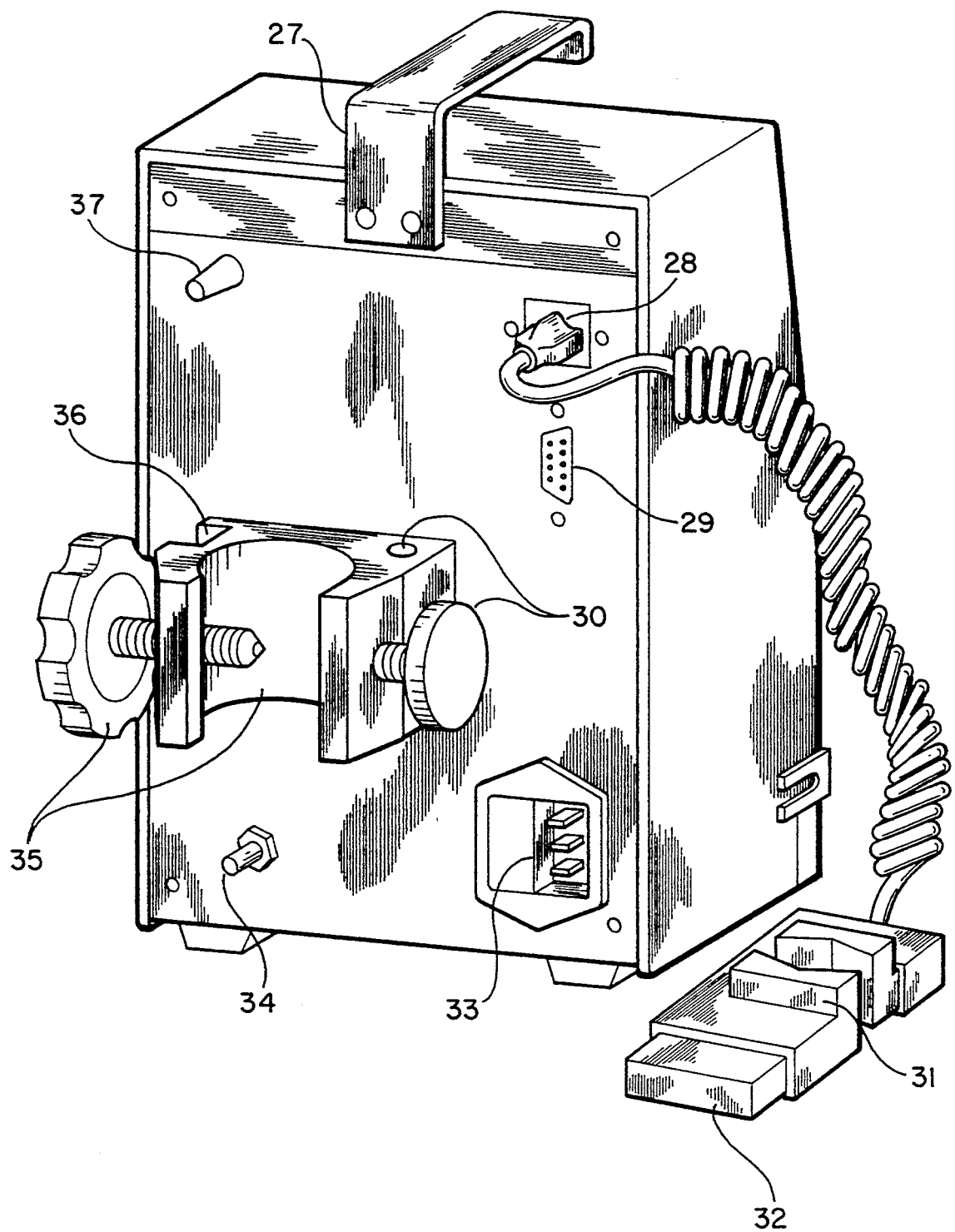
FIG. 3 provides a rear view of the preferred embodiment.

FIG. 3 shows the rear view of the preferred embodiment with a pump handle 27, a flow sensor plug 28, and a communications port 29. Also shown is a portable pole clamp 30, flow sensor risers 31, a flow sensor 32, an AC power source 33, a grounding screw 34, a pole clamp 35, a flow sensor bracket 36, and the alarm volume control 37. In the preferred embodiment, the flow sensor 32 comprises an infrared eye system. The flow sensor 32 counts the drops falling into the drip chamber. This can detect a variety of problems, including the wrong tubing being selected, the wrong fluid being selected, a leak in the system, an occlusion in the system, or an empty bag. For any selected tube type and fluid type, in a system without a leak or an occlusion and where the bag does not empty, a specific drop rate range would be tested for.

The pump handle 27 is used for transporting the pump. The flow sensor plug 28 receives the plug from the flow sensor's jack. The communications port 29 permits the exchange of information between the pump and a computer via cable or modem. The portable pole clamp 30 is used to attach an optional portable pole to the pump. The flow sensor risers 31 are used to position the flow sensor on the drip chamber. The flow sensor 32 attaches to the intravenous set's drip chamber to detect the fluid flow and to signal an alarm for an occlusion in the upper portion of the tube, for an empty bag, or for a high flow rate. The AC power socket 33 provides a 110 volt AC socket with a line fuse. The grounding screw 34 permits an external grounding wire to be attached to the pump if necessary. The pole clamp 35 is used to attach the pump to an intravenous administration set pole. The flow sensor bracket 36 is used to hold the flow sensor when it is not in use. The alarm volume control 37 is used to increase or decrease the audible alarm volume.

The piggyback delivery profile function of the present invention allows for the use of a second profile to be applied before, during an interrupt, or after the first profile. In addition to the first IV bag, a second IV bag may be hung higher up and inserted in a Y-joint intersection into the IV tube above the pump. With its superior pressure, the second bag's flow interrupts the flow from the first bag. The piggyback profile can then be selected to interrupt the delivery profile for the original bag. This allows a different medicine and a different fluid to be infused through the infusion pump on an interrupt basis. The memory of the pump remembers the status of the first delivery profile when it is interrupted by the piggyback profile, so that the first delivery profile may be resumed with the first fluid once the piggyback profile is delivered with the piggyback fluid.

The data from the pressure sensor 25, and flow sensor 32, the speed of the motor of the differential cam are all adjusted for the tube type being used and for the mechanical characteristics of the fluid being delivered, in order to deliver the selected profile. This is necessary to deliver the selected delivery profile given the parameters of the system characteristics being selected. This allows different delivery profiles to be delivered through different tubing types by one pump without any replacement of the mechanical parts of the pump.

Figure 4:
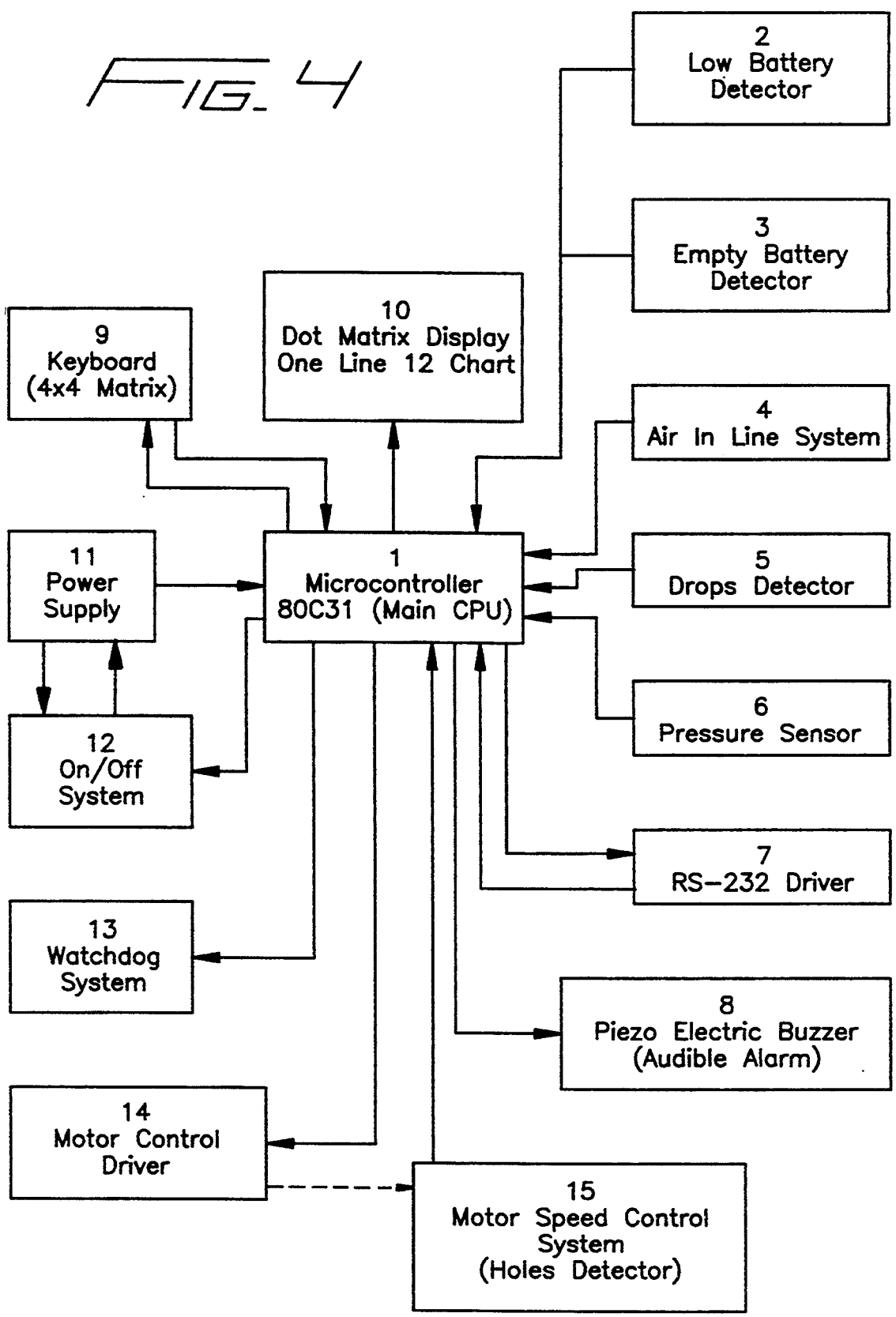
FIG. 4 shows the main block diagram schematically indicating the logic of the electronic circuitry of the present invention.

FIG. 4 shows the main block diagram schematically indicating the logic of the electronic circuitry of the present invention. The microcontroller 1 (the main CPU) in the infusion pump is based on the Intel TM 80C31 microcontroller which contains 2 timers, 2 external interrupts, 3 internal interrupts, 128K bytes of memory divided into two pages of 64K bytes each, 128 bytes of internal RAM, UART for communication (the same as the RS-232C communication standard), and 4 I/O ports.

The low battery detection 2 constantly monitors the battery's voltage giving a "1" logic to the CPU if the voltage is greater than 10 volts. If the voltage is between 9.5 volts and 10 volts, then the low battery detector will signal a "0" logic to the CPU. The CPU will then stop the motor, cause the words "LOW BATTERY" to appear on the pump's dot matrix display, and activate an audible alarm.

When a low battery is detected the only recourse available to the user are to connect the pump to AC line-power (to continue pump operation using AC power and to recharge the battery), or to resume pump operation using battery power.

If pump operation is resumed using battery power (i.e. without connecting the pump to AC line-power) and the CPU continues to receive a "0" logic signal from the low battery detector, the CPU will cause the words "LOW BATTERY" to appear on the pump's dot matrix display every 60 seconds for a period of 3 seconds and activate an audible alarm (concurrently with the visual alarm) every 60 seconds for a period of 3 seconds.

The empty battery detector 3 constantly monitors the battery's voltage giving a "1" logic to the CPU if the voltage is greater than 9.5 volts. If the voltage decreases to less than 9.5 volts, the empty battery detector will signal a "0" logic to the CPU. The CPU will then stop the motor, cause the words "EMPTY BATTERY" to appear on the pump's dot matrix display, and activate an audible alarm.

When an empty battery is detected the only recourse available to the user is to switch off the pump, connect the pump to AC line-power and then to turn the pump on.

The air-in-line detector 4 constantly monitors the status of the infusion set's tubing giving a "1" logic to the CPU when the section of tubing that passes through the air-in-line detector contains fluids only. If there is air (or an air bubble) in the section of tubing that passes through the air-in-line detector or if there is no tubing positioned in the air-in-line detector, the air-in-line detector will signal a "0" logic to the CPU. The CPU will then stop the motor, cause the words "AIR-IN-LINE" to appear on the pump's dot matrix display, and activate an audible alarm.

When an attempt is made to resume pump operation following the detection of air-in-line, the CPU first checks the logic received from the air-in-line detector. If a "1" logic is received by the CPU, the infusion will resume. If a "0" logic is received by the CPU, the pump's motor will not restart, the words "AIR-IN-LINE" will reappear on the pump's dot matrix display, and the audible alarm will be reactivated.

The drops detector (flow sensor) 5 detects every drop that falls through the drip chamber of the infusion set. The drops detector is based on an infra-red transmitter and a photo-transistor receiver. When a falling drop breaks the infra-red beam, the drops detector sends a pulse to the CPU's external interrupt number 0.

The pressure sensor 6 monitors, non-intrusively, the pressure within a section of the infusion set's tubing (the monitored section of tubing is pressed against the pressure sensor by the pump's door). The pressure sensor produces analog data which is converted into frequency (using a voltage control oscillator) and then sent to an internal counter in the CPU.

The RS-232 driver 7 functions as a power supply for the +12 volts and −12 volts that are necessary for the RS-232C communication standard.

The pizo-electric buzzer (audible alarm) 8 will sound a continuing intermittent beep when the audible alarm is initiated by the CPU, a beep whenever one of the keyboard's keys is pressed (i.e. an audible feedback for a pressed key), and a continuing clicking during the pump motor operation when the pump is being calibrated.

The keyboard 9 is the input terminal for entering information. The keyboard has 15 single-function and multi-function keys, including 10 keys numbered 0 through 9 (single function), a RUN/HOLD key (multi-function), a TIME/PIGGYBACK key (multi-function), a PRESSURE key (multi-function), a ON/OFF key (single-function), a YES key (multi-function), and a NO key (multi-function). The CPU constantly scans the keyboard to detect if any key is pressed.

The dot matrix display 10 consists of three LED smart displays each displaying up to 4 characters (with a total of 12 characters). The CPU sends each display the desired characters's ASCII code as well as the desired character's position on the display screen. The CPU also controls the dot matrix display's brightness by sending an appropriate signal to the display.

The power supply 11 converts the AC line-power to a DC current. The power supply produces three different voltages: 5 volts (regulated voltage), 12 volts (regulated voltage), and approximately 12 volts (unregulated voltage).

When the ON/OFF key on the on/off system 12 is pressed, a pulse is sent to the on/off system which then relays that information to the power supply. The ON/OFF key is controlled separately from the other keys on the keyboard.

The watchdog system 13 monitors impulses from the software to detect if the software is functioning properly. If the watchdog system detects that the software is not functioning properly, it disconnects power supply to the motor, and it illuminates the CPU indicator LED on the front panel.

The CPU sends the motor control drive 14 a digital code containing information on the desired motor speed. The motor control driver converts the digital code received from the CPU into analog data which is then sent to the power operational amplifier (op-amp). The power op-amp changes the motor speed by varying the voltage and current sent to the motor. The voltage and current sent to the motor are determined by the analog data that the power op-amp has received from the motor control driver.

The motor speed control (encoder-disk detector) 15 which has ten holes evenly-spaced in a circle, is mounted on the end of the motor shaft. Each full turn of the shaft represents ten equal steps (36 degrees for each step). The motor speed control is based on a photo-interrupter (an optical device) which sends a pulse to the external interrupt number 1 of the CPU each time it detects an encoder-disk hole, thus providing the CPU with verification of the motor speed.

Figure 5:
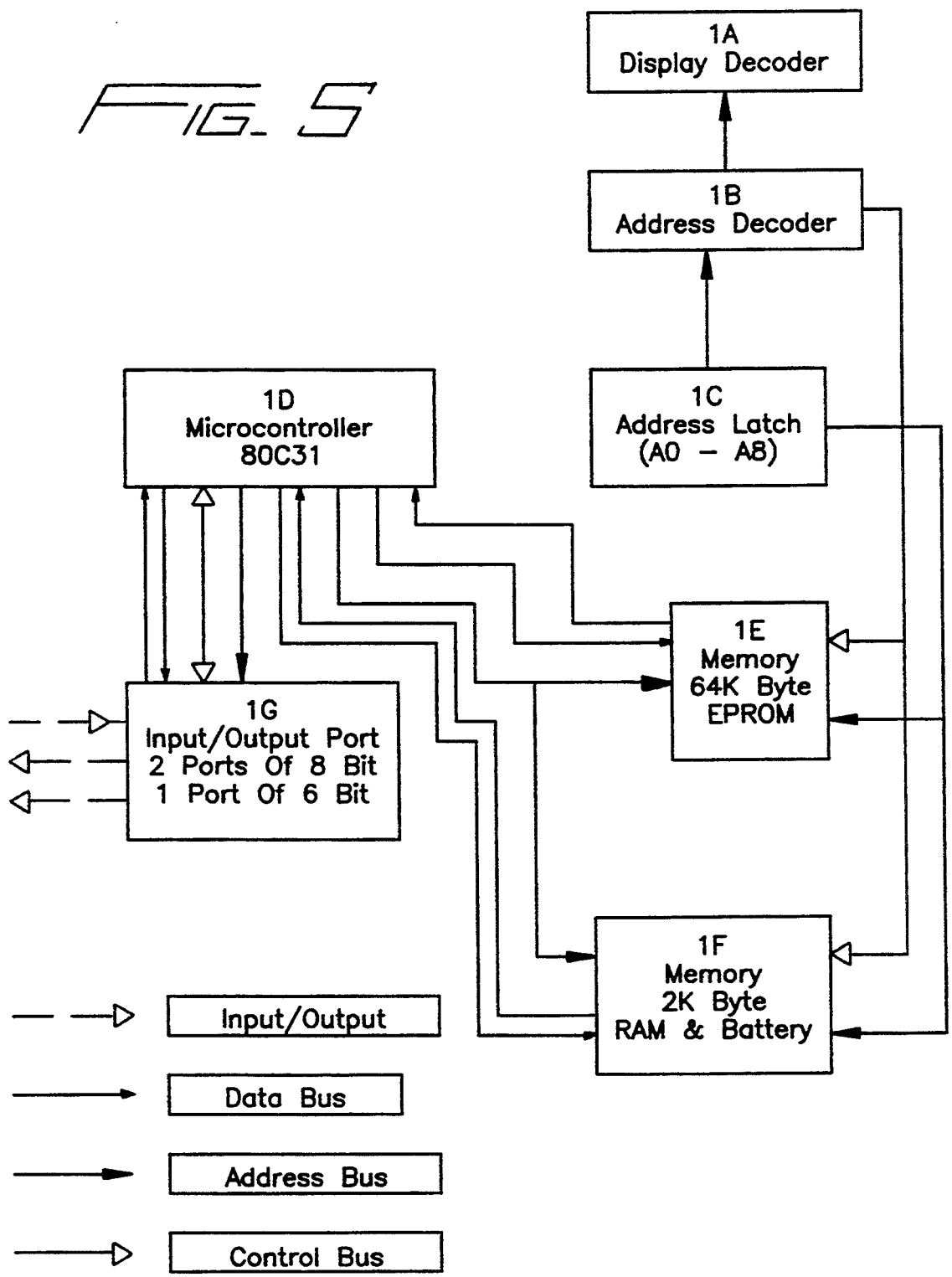
FIG. 5 shows further detail of block 1 of FIG. 4, the microcontroller.

FIG. 5 shows further detail of block 1 of FIG. 4, the microcontroller. FIG. 5 shows schematically the logic of the microcontroller.

The display decoder 1A receives an address from the CPU via the address decoder 1B and relays the data to the corresponding address of each of the three smart displays.

The address decoder 1B decodes the address sent from the CPU via the address bus and then routes it to the appropriate component. The address decoder provides the chip selection for each component.

The address latch 1C latches the low address buses (A0 through A7) whenever the CPU requires data from an external component (such as an EPROM, RAM, PIA).

The infusion pump is based on the Intel ™ 80C31 microcontroller 1D which contains 2 timers, 2 external interrupts, 3 internal interrupts, 128K bytes of memory divided into two pages of 64K bytes each, 128 bytes of internal RAM, UART for communication (the same as the RS-232C communication standard), and 4 I/O ports.

The 64K byte EPROM 1E stores all the software. There is a routine that checks the EPROM (a checksum) whenever the pump is switched on.

The RAM's 2 byte memory 1F is backed-up by the RAM's internal battery. The RAM stores important pump information (such as calibration parameters, infusion parameters, and the tubing specification table). There is a routine that checks the RAM whenever the pump is switched on.

The P.I.A. (Programmable Interface Adaptor) 1G is an expansion component that provides additional input/output ports used to control all the sub-systems located on the main pcb. These ports include:

| | | |
|---|---|---|
| Port A (8 bits): | * | PA.0 to PA.3 is the code for the motor driver. |
| | | PA.7 is the enable for the air-in-line detector. |
| Port B (8 bits): | * | PB.0 to PB.3 is the output that scans the keyboard. |
| Port C (6 bits): | * | PC.0 to PC.3 is the input from the keyboard. |
| | * | PC.5 is the input from the empty battery detector. |

The embodiments as illustrated and discussed in this specification are intended only to teach those skilled in the art the best way known by the inventor to make and use the invention. Nothing in the specification should be considered as limiting the scope of the present invention. Many changes could be made by those skilled in the art to produce equivalent systems without departing form the invention. The present invention should be limited only by the following claims and their legal equivalents.

Figure 6:
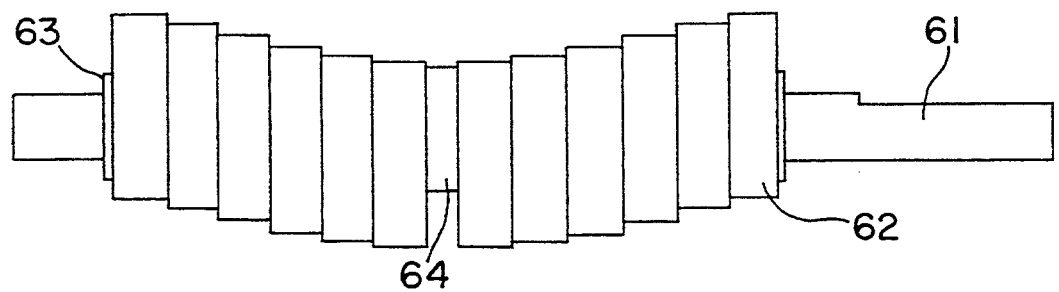
FIG. 6 shows a side view of the rotating differential cam.
Figure 7:
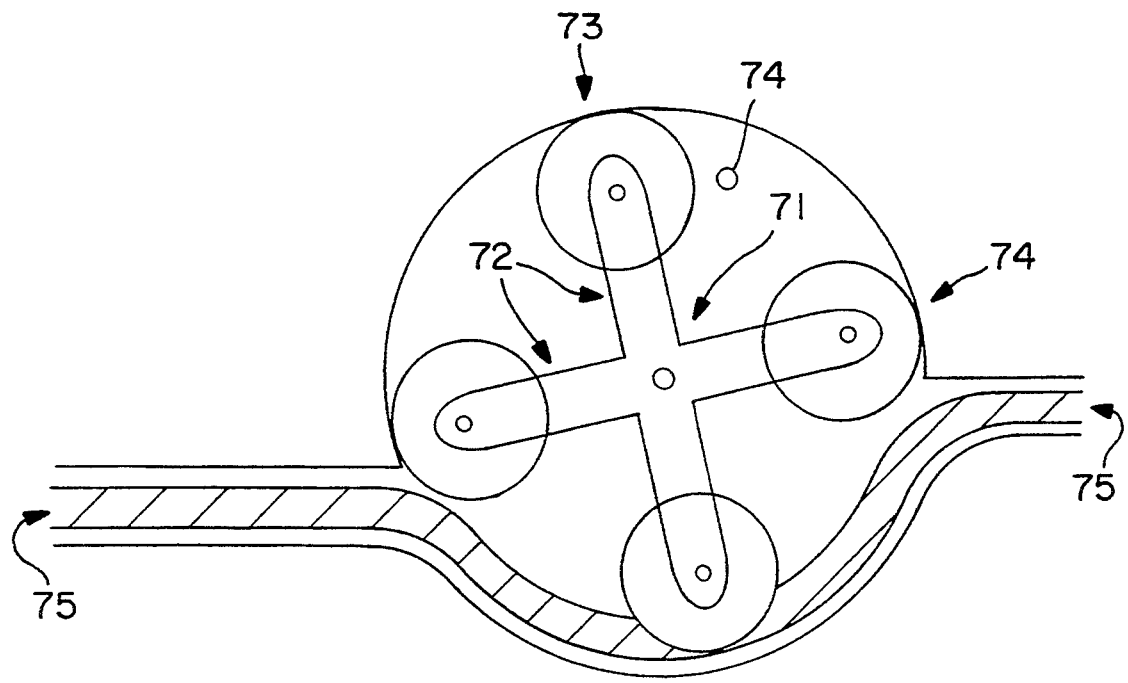
FIG. 7 shows a side view of the rotor with a plurality of arms, inside a chamber.

For example the peristaltic finger pump elements with the revolving differential cam in the preferred embodiment can be replaced in equivalent embodiments by peristaltic rotary pump elements, with a rotor with a plurality of arms, each arm having a roller attached to the end thereof, which rotor rotates inside of a chamber, the outer walls of which chamber contain an IV infusion tube such that the rollers of the rotating rotor in the chamber compress the tube in a series of constrictions moving through the tube in a peristaltic manner. FIG. 6 shows the preferred embodiment of the revolving differential cam with the main motor shaft 61, the peristaltic ring 62, the clip 63 holding the rings fixed onto the shaft, and the middle spacer 64. FIG. 7 shows the preferred embodiment of the rotor in the chamber with the rotor 71, the arms 72, a roller 73 at the end of each arm, the chamber 74, and the tube 75.

We claim:
1. An infusion pump comprising:
 a. A variable speed motor,
 b. Means to pump fluid through an intravenous tube into a patient, said pump means mechanically connected to and powered by the variable speed motor,
 c. Means for inputting information describing an initial type and size of an IV tube, and a fluid delivery profile,
 d. Means to calculate the motor speed profile which is recalibratable for different initial tube types and sizes as required to achieve the described fluid delivery profile for the described initial tube type and size, said calculation means electrically communicating with said means for inputting information describing an initial tube type and size, and a fluid delivery profile, and
 e. Means to control the motor according to the motor speed profile, said control means electrically communicating with said calculation means.

2. The device in claim 1 where the means to pump the fluid comprises twelve fingers depressed in a peristaltic series against an intravenous tube to create peristaltic contractions in the tube, the fingers being depressed by a rotating differential cam attached to the fingers, the cam being rotated by the variable speed motor.

3. The device in claim 1 further comprising a means for sensing occlusion in the tube, which means comprises a pressure sensor for the tube pressed against the tube, and said means electrically communicating with the means to calculate the motor speed profile.

4. The device in claim 3, where the pressure sensor is a strain gauge pressed against the tube.

5. The invention in claim 1 where the means for inputting information describing the initial IV tube type and size and the fluid delivery profile further comprises a keyboard, electrically communicating with said means for calculating.

6. The invention in claim 1, where the means to calculate the motor speed profile comprises:
 a. An integrated circuit chip with a memory and a calculating function, the memory containing data regarding the general shapes and calculation methods of a plurality of possible fluid delivery profile types, and a plurality of possible tube types to use for infusion.

7. The invention in claim 6 where the plurality of fluid delivery profile types further comprises:
   a. a first profile type having a fixed rate of fluid flow,
   b. a second profile type having a ramp up of steadily increasing flow rate,
   c. a third profile type having a fixed base flow rate with increased rate spikes at intervals,
   d. a fourth profile type having a base flow rate fixed at zero with increased rate spikes at intervals, and
   e. a fifth profile type having a ramp down of steadily decreasing flow rate.

8. The invention in claim 1 where the means to control the motor comprises:
   a. A solid state motor controller.

9. The invention in claim 1 where the means to pump fluid through the tube comprises:
   a. A rotor with a plurality of arms, each arm having a roller attached to the end thereof, which rotor rotates inside of a chamber, the outer walls of which chamber contain the IV tube such that the rollers of the rotating rotor in the chamber compress the tube in a series of constrictions moving through the tube in a peristaltic manner.

* * * * *